United States Patent
Shimada et al.

(10) Patent No.: US 10,531,849 B2
(45) Date of Patent: Jan. 14, 2020

(54) RADIOGRAPHIC IMAGING APPARATUS, RADIOGRAPHIC IMAGING SYSTEM, RADIOGRAPHIC IMAGING METHOD, AND STORAGE MEDIUM

(71) Applicant: CANON KABUSHIKI KAISHA, Tokyo (JP)

(72) Inventors: Tetsuo Shimada, Hachioji (JP); Osamu Tsujii, Kawasaki (JP); Akira Yoshino, Tokyo (JP); Hidehiko Morinaga, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 231 days.

(21) Appl. No.: 15/625,207

(22) Filed: Jun. 16, 2017

(65) Prior Publication Data

US 2017/0367669 A1 Dec. 28, 2017

(30) Foreign Application Priority Data

Jun. 22, 2016 (JP) ................. 2016-123372

(51) Int. Cl.
*G01T 1/20* (2006.01)
*A61B 6/00* (2006.01)
*A61B 6/03* (2006.01)

(52) U.S. Cl.
CPC .............. *A61B 6/463* (2013.01); *A61B 6/032* (2013.01); *A61B 6/4417* (2013.01); *A61B 6/465* (2013.01); *A61B 6/502* (2013.01); *A61B 6/54* (2013.01)

(58) Field of Classification Search
CPC ......... A61B 6/463; A61B 6/032; A61B 6/035; A61B 6/0414; A61B 6/08; A61B 6/4417; A61B 6/4435; A61B 6/488; A61B 6/502; A61B 6/5235; A61B 6/54; A61B 5/0035; A61B 5/0077; A61B 5/7425; A61B 6/486;

(Continued)

(56) References Cited

U.S. PATENT DOCUMENTS 5,982,917 A * 11/1999 Clarke .................. G06T 7/0012
128/922
9,146,663 B2 * 9/2015 Kreeger ................ G06F 19/321

(Continued)

FOREIGN PATENT DOCUMENTS

JP 2013538668 A 10/2013
JP 2015073657 A 4/2015

*Primary Examiner* — Kiho Kim
(74) *Attorney, Agent, or Firm* — Canon U.S.A., Inc. IP Division

(57) ABSTRACT

There is provided a radiographic imaging apparatus capable of facilitating a comparative radiological interpretation of symmetric portions or a temporal comparative radiological interpretation of a same imaging target. The radiographic imaging apparatus includes an image control unit configured to cause a display unit configured to display a plurality of divided screens to display a first radiographic image of a first imaging target on a first divided screen of the plurality of divided screens. The image control unit causes a radiographic image of the first imaging target that is captured at a different time from the first radiographic image or a radiographic image of a second imaging target that is a symmetric imaging target of the first imaging target to be displayed on a second divided screen of the plurality of divided screens as a second radiographic image.

13 Claims, 11 Drawing Sheets

(58) Field of Classification Search
CPC .......... A61B 6/465; G06T 2207/30068; H04N 5/44591
See application file for complete search history.

(56) References Cited

U.S. PATENT DOCUMENTS

| | | | | |
|---|---|---|---|---|
| 2001/0038707 | A1* | 11/2001 | Ohara | A61B 6/4233 |
| | | | | 382/132 |
| 2003/0212327 | A1 | 11/2003 | Wang | |
| 2006/0029268 | A1* | 2/2006 | Endo | A61B 6/463 |
| | | | | 382/132 |
| 2006/0098855 | A1* | 5/2006 | Gkanatsios | A61B 5/0048 |
| | | | | 382/128 |
| 2008/0019581 | A1* | 1/2008 | Gkanatsios | A61B 6/025 |
| | | | | 382/131 |
| 2012/0043963 | A1* | 2/2012 | Rapoport | A61B 5/0073 |
| | | | | 324/307 |
| 2015/0086103 | A1* | 3/2015 | Tsunomori | G06T 7/0012 |
| | | | | 382/133 |
| 2015/0230770 | A1 | 8/2015 | Heinlein | |
| 2015/0250440 | A1* | 9/2015 | Sugahara | A61B 6/502 |
| | | | | 378/37 |

* cited by examiner

RADIOGRAPHIC IMAGING APPARATUS, RADIOGRAPHIC IMAGING SYSTEM, RADIOGRAPHIC IMAGING METHOD, AND STORAGE MEDIUM

BACKGROUND OF THE INVENTION

Field of the Invention

The present invention relates to a radiographic imaging system, a radiographic imaging method, and a storage medium, and, in particular, to a radiographic imaging system, a radiographic imaging method, and a storage medium for imaging a breast with use of radiation.

Description of the Related Art

As breast imaging apparatuses, there are apparatuses that image a breast with use of a radiation generation unit configured to generate radiation and a radiation detection unit configured to detect the radiation.

Further, some techniques allow the same breast imaging apparatus to carry out both of mammographic imaging and computed tomographic (CT) imaging (e.g., Japanese Unexamined Patent Application Publication (Translation of PCT Application) No. 2013-538668).

The conventional CT apparatuses specialized for breasts are not equipped with a function of, when imaging left and right breasts individually, referring to position adjustment information of a breast imaged first (e.g., the left breast) to adjust a position of a breast imaged after that (e.g., the right breast on an opposite side from the left breast).

Further, in the conventional CT imaging apparatuses, a screen is displayed on an operation screen of an operation unit each time a target portion is imaged once, and a previous imaging condition such as a fixation position and an exposure condition employed at the time of previous imaging of the same portion is not displayed at the same time.

Therefore, an operator should select a plurality screens with use of a hierarchy and separately display them when mutually referring to symmetric left and right portions or referring to the imaging condition employed at the time of the previous imaging of the same portion. Therefore, the operator should perform cumbersome operations.

SUMMARY OF THE INVENTION

According to an aspect of the present invention, a radiographic imaging apparatus includes an image control unit configured to cause a display unit that displays a plurality of divided screens thereon to display a first radiographic image of a first imaging target on a first divided screen of the plurality of divided screens. The image control unit causes a radiographic image of the first imaging target that is captured at a different time from the first radiographic image or a radiographic image of a second imaging target that is a symmetric portion of the first imaging target to be displayed on a second divided screen of the plurality of divided screens as a second radiographic image.

Further features of the present invention will become apparent from the following description of exemplary embodiments with reference to the attached drawings. Each of the embodiments of the present invention described below can be implemented solely or as a combination of a plurality of the embodiments or features thereof where necessary or where the combination of elements or features from individual embodiments in a single embodiment is beneficial.

DESCRIPTION OF THE EMBODIMENTS

Figure 1:
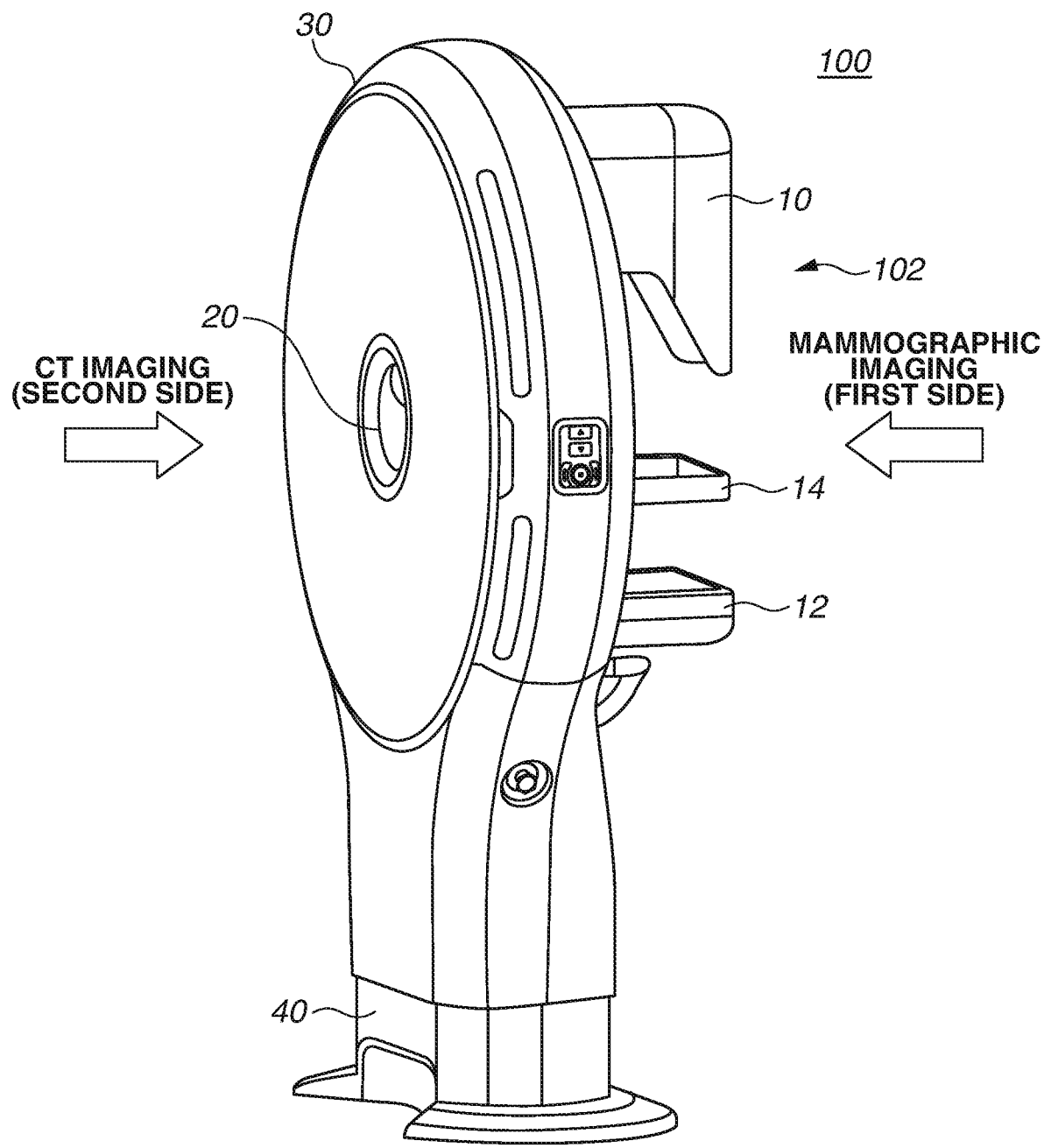
FIG. 1 illustrates an outer appearance of a radiographic imaging apparatus according to an exemplary embodiment of the present invention.

FIG. 1 illustrates an outer appearance of a breast imaging apparatus (radiographic imaging apparatus) 100 according to an exemplary embodiment of the present invention. The breast imaging apparatus 100 can carry out mammographic imaging and CT imaging.

A radiographic imaging system including the breast imaging apparatus 100 includes a radiation generation unit configured to generate radiation, and a radiation detection unit 12 configured to detect the radiation, generated by the radiation generation unit 10, with which a subject is irradiated. Further, the radiographic imaging system including the breast imaging apparatus 100 includes a gantry (rotational unit) 30 capable of rotating the radiation generation unit 10 and the radiation detection unit 12 facing each other. An imaging unit 102 mainly includes the radiation generation unit 10 and the radiation detection unit 12.

Then, an imaging target (or portion, e.g. a breast) of the subject is imaged while being sandwiched by a pressing plate 14 from a first side of the breast imaging apparatus 100. A grid (not illustrated) may be provided on a top surface of the radiation detection unit 12, and the imaging target (breast) of the subject may be imaged while being sandwiched between the pressing plate 14 and the grid. In other words, the breast imaging apparatus 100 includes a first imaging unit of a mammographic imaging mode.

The imaging target (breast) of the subject is imaged while the radiation generation unit 10 and the radiation detection unit 12 are rotated in such a state that this imaging target is fixed in a breast holding portion 34 after being inserted into between the radiation generation unit 10 and the radiation detection unit 12 via an opening 20 from a second side opposite from the first side of the breast imaging apparatus 100. In other words, the breast imaging apparatus 100 includes a second imaging unit of a CT imaging mode.

The breast imaging apparatus 100 includes the gantry 30 that rotatably supports the radiation generation unit 10 and the radiation detection unit 12, and a support leg portion 40 that supports the gantry 30 with respect to a floor surface. In other words, the gantry 30 rotatably supports the imaging unit 102.

When the mammographic imaging is carried out, the imaging target (breast) of the subject is imaged while being sandwiched between the pressing plate 14 and the radiation detection unit 12 from the first side (right side in FIG. 1) of the breast imaging apparatus 100. The pressing plate 14 is a transparent material, and that permits the radiation to be transmitted therethrough. More specifically, the breast of the subject can be sandwiched between the pressing plate and the radiation detection unit 12 by vertically displacing the pressing plate 14.

The radiation generation unit 10 generates the radiation with the breast of the subject sandwiched between the pressing plate 14 and the radiation detection unit 12. The radiation detection unit 12 can image the breast of the subject by detecting the radiation transmitted through the breast of the subject. The breast imaging apparatus 100 can generate a mammographic image based on captured radiation data.

When the CT imaging is carried out, the imaging target (breast) of the subject is inserted into between the radiation generation unit 10 and the radiation detection unit 12 via the opening 20 from the second side (left side in FIG. 1) opposite to the first side of the breast imaging apparatus 100, and is fixed in the breast holding portion 34. Then, the image is captured while the radiation generation unit 10 and the radiation detection unit 12 are rotated in this state. While the radiation generation unit and the radiation detection unit 12 are rotated by a rotational frame 38, the radiation is generated by the radiation generation unit 10.

The radiation detection unit 12 can image the breast of the subject by detecting the radiation transmitted through the breast of the subject. The breast imaging apparatus 100 can generate a CT image by reconstructing captured radiation data.

Figure 2:
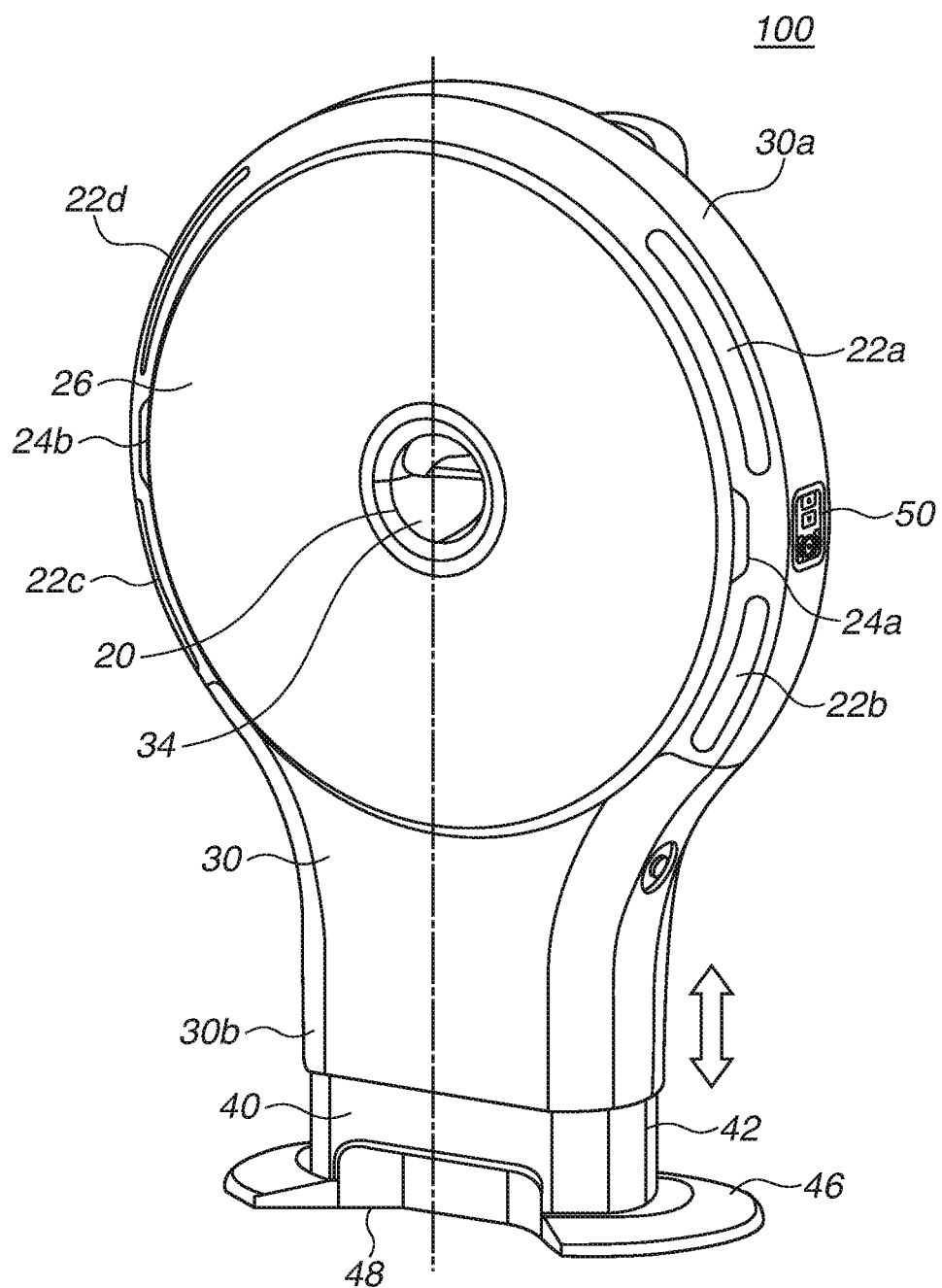
FIG. 2 illustrates an outer appearance of the radiographic imaging apparatus according to the exemplary embodiment of the present invention as viewed from a computed tomographic (CT) imaging side.
Figure 3:
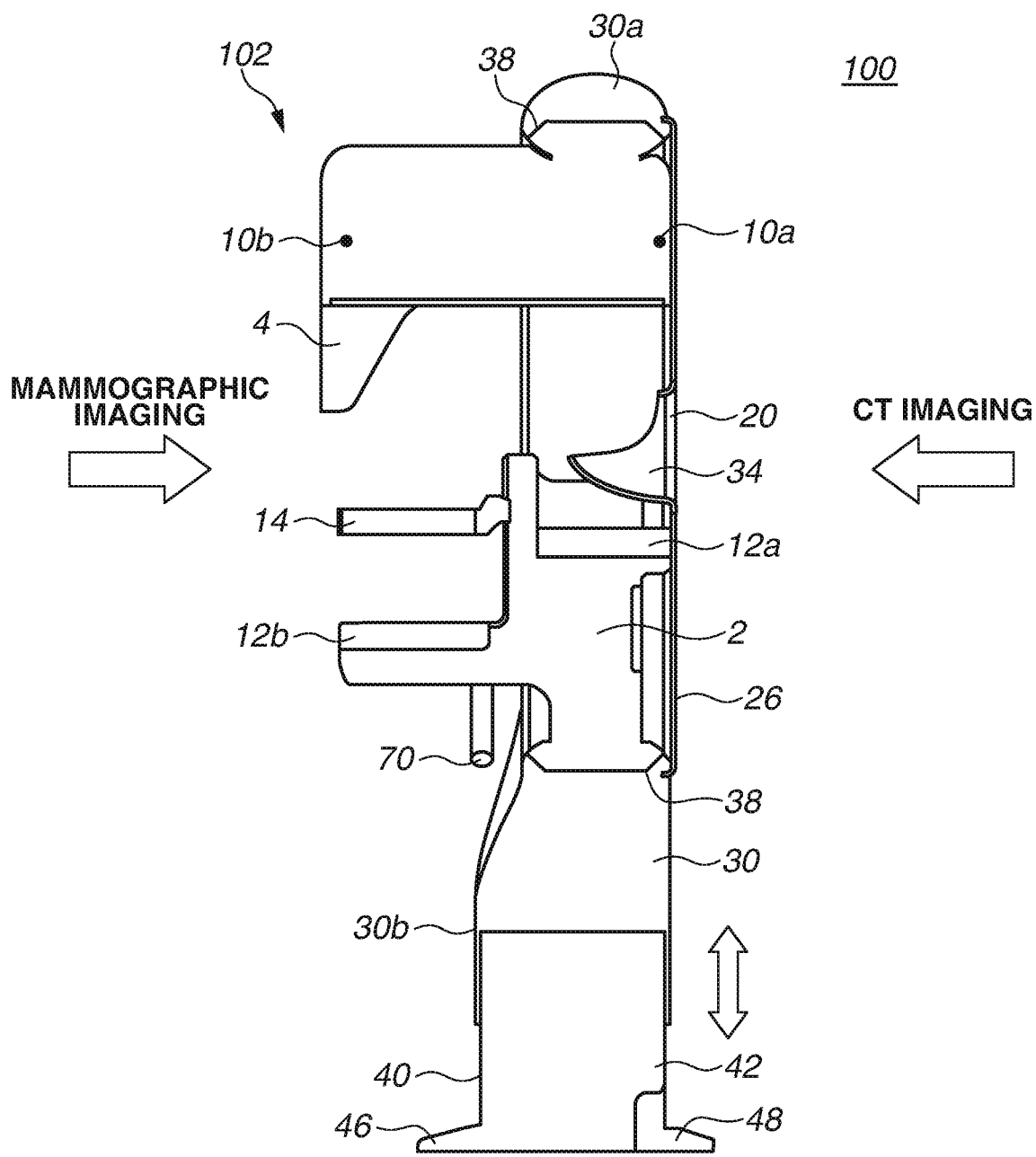
FIG. 3 is a cross-sectional view of the radiographic imaging apparatus according to the exemplary embodiment of the present invention.
Figure 4:
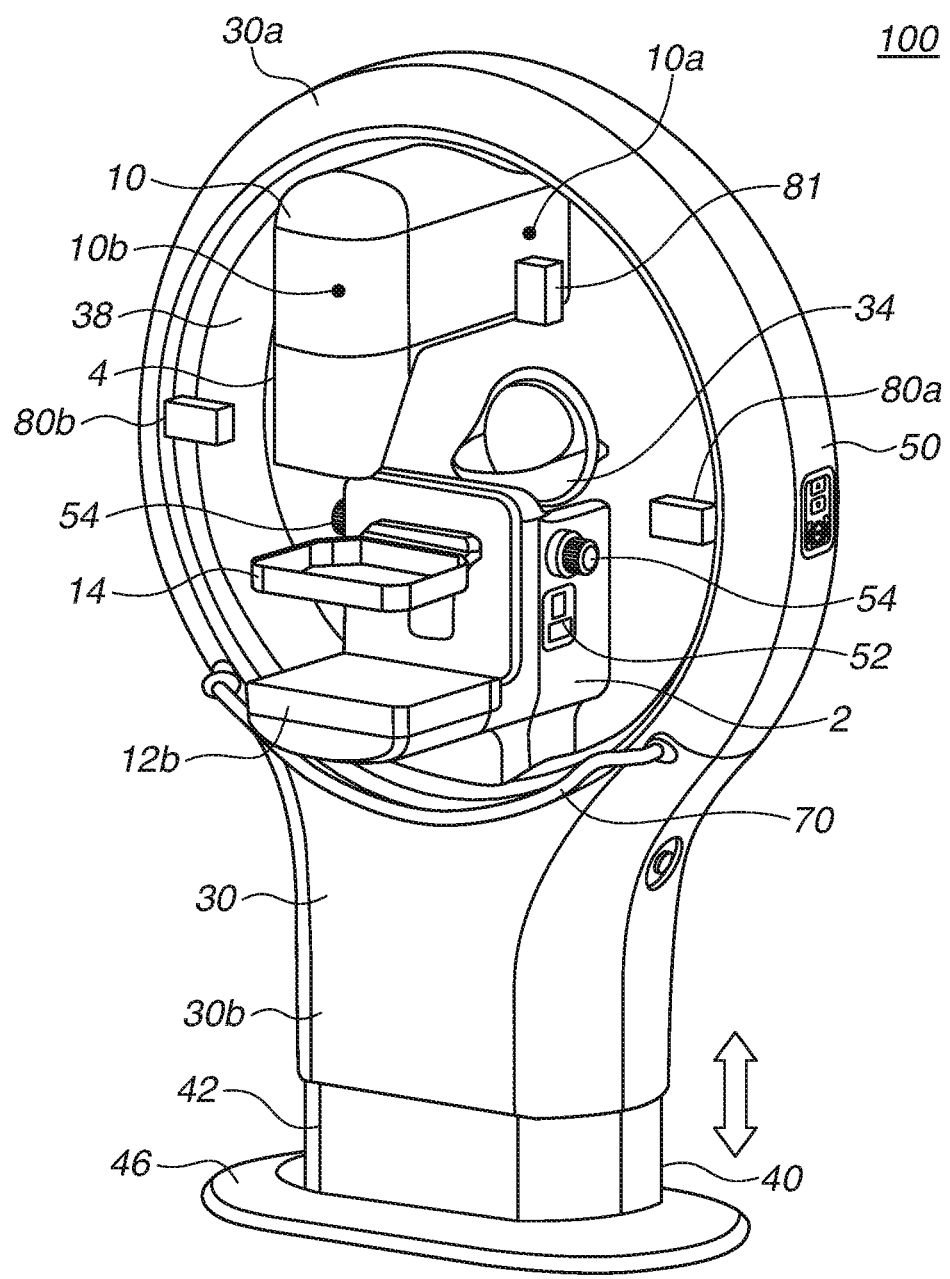
FIG. 4 illustrates an outer appearance of the radiographic imaging apparatus according to the exemplary embodiment of the present invention as viewed from a mammographic imaging side.

Now, the breast imaging apparatus 100 will be described specifically with reference to FIGS. 2 to 4. FIG. 2 illustrates an outer appearance of the breast imaging apparatus 100 as viewed from a CT imaging side. FIG. 3 is a cross-sectional view of the breast imaging apparatus 100. The cross-sectional view of the breast imaging apparatus 100 is a cross-sectional view taken along a central line (alternate long and short dash line) extending in a vertical direction of the breast imaging apparatus 100 illustrated in FIG. 2. FIG. 4 illustrates an outer appearance of the breast imaging apparatus 100 as viewed from a mammographic imaging side.

As illustrated in FIG. 2, which protects the subject from the radiation generation unit 10 and the radiation detection unit 12 rotated at the time of the CT imaging, is placed on the gantry 30 on the CT imaging side.

The front cover 26 includes the opening 20 for inserting the breast of the subject who is subjected to the CT imaging.

Further, a plurality of gripping portions 22a, 22b, 22c, and 22d, which is used for the subject subjected to the CT imaging to hold, is provided at the gantry 30 on the CT imaging side. The plurality of gripping portions 22a, 22b, 22c, and 22d is each formed into a recessed shape. Further, a cutout portion 48, which is used for the subject subjected to the CT imaging to insert subject's legs therein, is provided at a base 46 at the support leg portion 40 on the CT imaging side.

As illustrated in FIG. 4, the pressing plate 14, which presses the breast of the subject subjected to the mammographic imaging, is mounted on the gantry 30 on the mammographic imaging side. Further, a protection plate 4, which is used to protect the subject from an unnecessary exposure, is mounted on the gantry 30 on the mammographic imaging side. Further, a gripping portion 70, which is used for the subject subjected to the mammographic imaging to hold, is provided on the gantry 30 on the mammographic imaging side. The gripping portion 70 is formed into a protruding shape.

Figure 5:
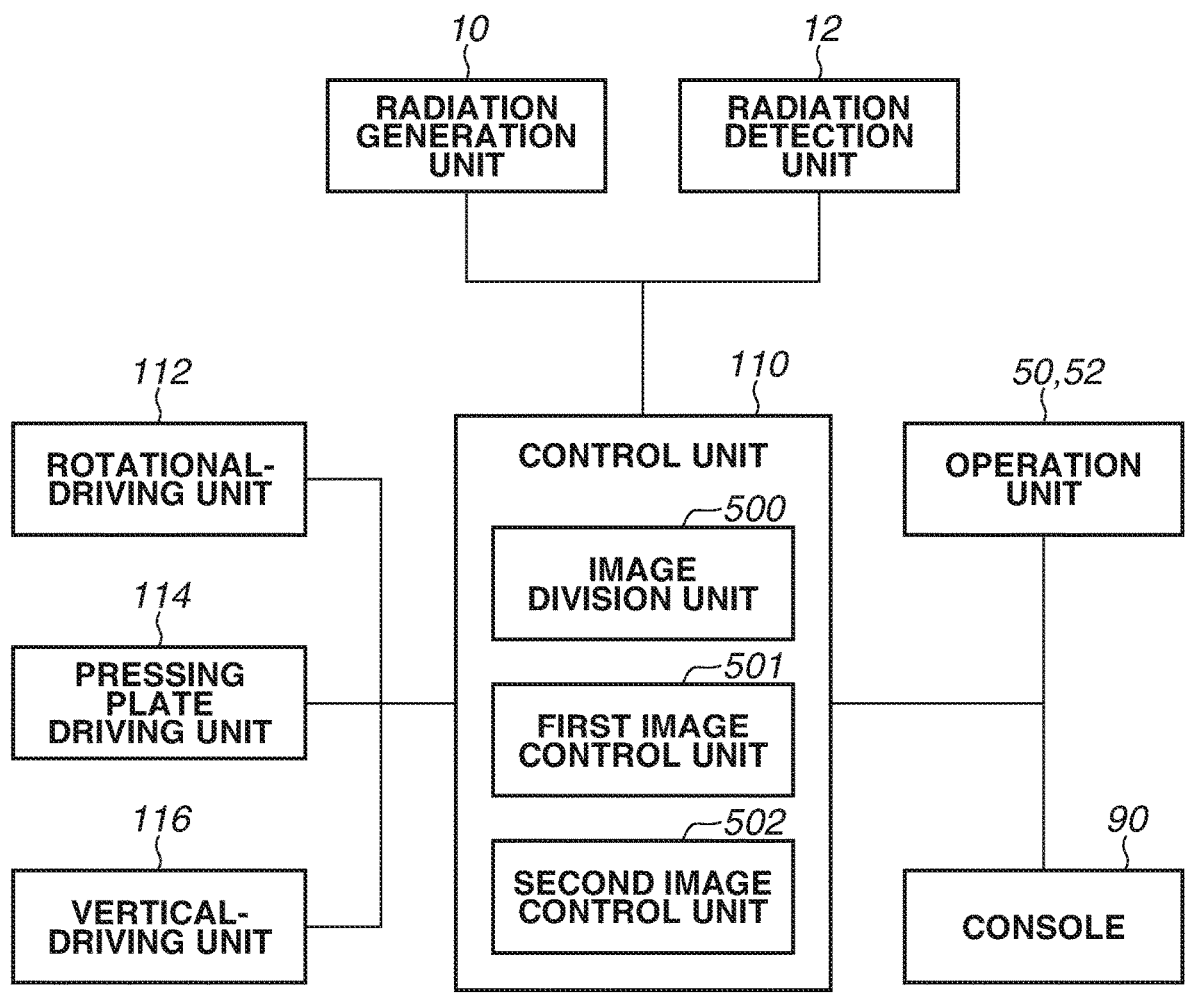
FIG. 5 illustrates a configuration of the radiographic imaging apparatus according to the exemplary embodiment of the present invention.

FIG. 5 illustrates a configuration of the breast imaging apparatus 100. The breast imaging apparatus 100 includes a rotational-driving unit 112 configured to rotate the radiation generation unit 10 and the radiation detection unit 12 with the radiation generation unit 10 and the radiation detection unit 12 facing each other. Further, the breast imaging apparatus 100 includes a pressing plate driving unit 114 configured to vertically displace the pressing plate 14, and a vertical-driving unit 116 configured to vertically displace the gantry 30 relative to the support leg portion 40.

The breast imaging apparatus 100 includes a control unit 110 configured to individually control the radiation generation unit 10, the radiation detection unit 12, the rotational-driving unit 112, the pressing plate driving unit 114, and the vertical-driving unit 116. The control unit (an image control unit) 110 includes an image division unit 500, a first image control unit 501, and a second image control unit 502.

Further, the breast imaging apparatus 100 includes operation units 50 and 52 and a console 90 for transmitting an instruction to the control unit 110. The operation unit 50, which is used to operate the breast imaging apparatus 100, is disposed at the gantry 30, and the operation unit 52, which has a similar function to the operation unit 50, is disposed on a support base 2 supporting the radiation detection unit 12. Further, the console 90 is set up outside an imaging room.

Further, a display unit configured to display any one of the subject information, height information of a radiation detection unit 12b, dose information of the radiation generation unit 10, and pressing information (N) pressed by the pressing plate 14, may be disposed on the support base 2.

The radiation generation unit 10 includes an electron emission source that mainly generates electrons, and a target, although they are not illustrated. The electrons generated at the electron emission source are emitted toward a target side due to a potential difference between a cathode and an anode. The target is a member that generates the radiation with the aid of a collision therewith. The radiation radiated from the target is shaped into a cone-beam shape and emitted outward. The control unit 110 can control imaging conditions of the radiation generation unit 10.

The radiation detection unit 12 functions to detect the radiation transmitted through the subject by a photoelectric conversion element and output the detected radiation as an electric signal. For example, the radiation detection unit 12 includes a conversion panel for detecting the radiation transmitted through the subject, an electric charge storage unit, an interface (I/F) for outputting the information converted from the radiation into the electric signal, and the like. The radiation detection unit 12 outputs the electric signal to the control unit 110 via the I/F.

<Gantry>

As illustrated in FIGS. 2 to 4, the gantry 30 includes the ring-shaped rotational frame 38 for rotating the radiation generation unit 10 and the radiation detection unit 12 facing each other, and a ring-shaped fixed frame 30a that rotatably supports the rotational frame 38. The fixed frame 30a may have a circular-arc shape, and rotatably support a part of the rotational frame 38. Further, the gantry 30 includes an elongated cylindrical portion 30b coupled to the fixed frame 30a and having an elongated cylindrical shape.

The rotational frame 38 and the fixed frame 30a can also be referred to as a rotational unit configured to rotate the radiation generation unit 10 and the radiation detection unit 12. The fixed frame 30a and the elongated cylindrical portion 30b are integrally formed. The fixed frame 30a is positioned on a more upper side than the elongated cylindrical portion 30b. The elongated cylindrical portion 30b is coupled to the support leg portion 40 supporting the gantry 30 with respect to the floor surface.

The gantry 30 is erected in the vertical direction so as to allow the subject to be imaged in an upright position. A rotational axis of the rotational unit (the rotational frame 38 of the gantry 30) that rotates the radiation generation unit 10 and the radiation detection unit 12 extends in a horizontal direction.

The elongated cylindrical portion 30b covers an outer periphery of an elongated cylindrical portion 42 of the support leg portion 40. More specifically, the support leg portion 40 and the gantry 30 are configured in such a manner that the elongated cylindrical portion 42 of the support leg portion 40 is inserted inside the elongated cylindrical portion 30b of the gantry 30, and the elongated cylindrical portion 42 of the support leg portion 40 and the elongated cylindrical portion 30b of the gantry 30 are coupled to each other by a nesting structure.

Figure 6:
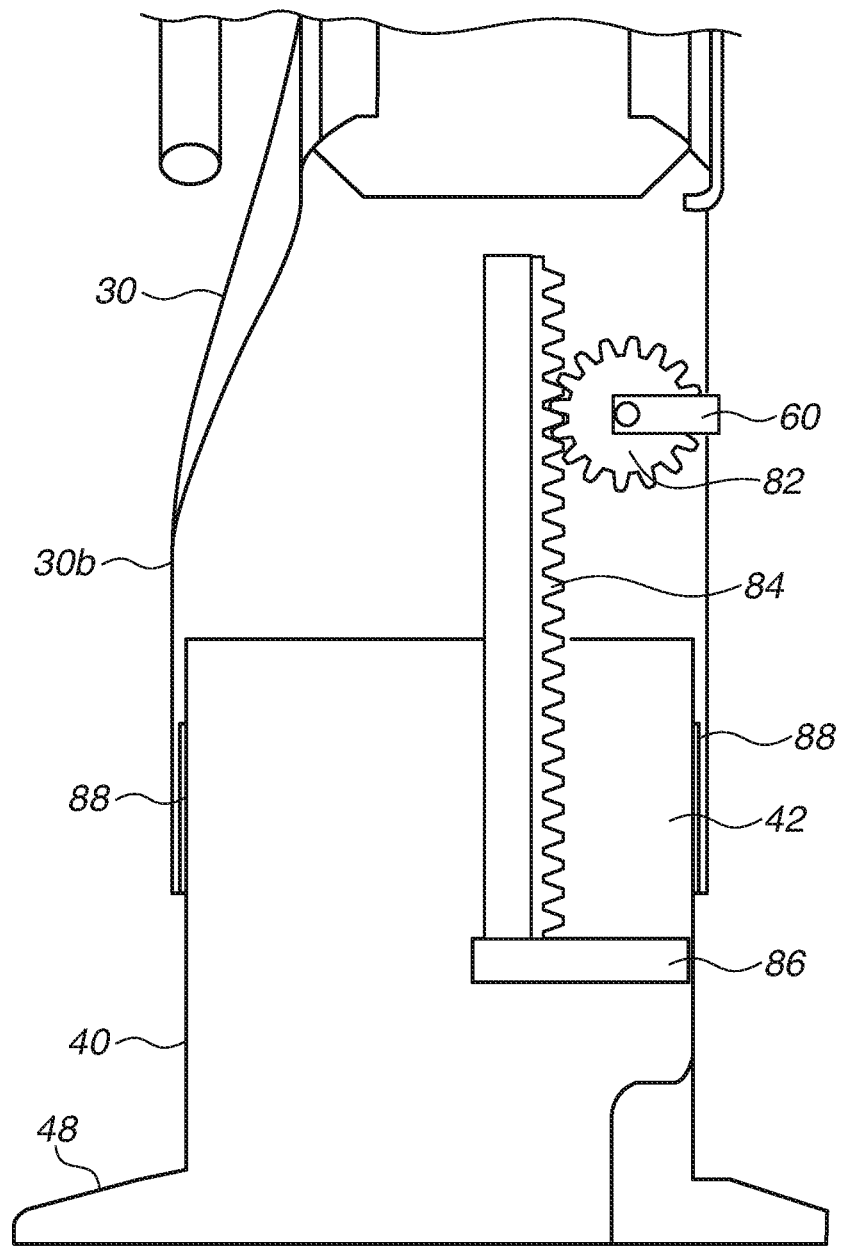
FIG. 6 illustrates a configuration of a vertical-driving unit of the radiographic imaging apparatus according to the exemplary embodiment of the present invention.

As illustrated in FIG. 6, the breast imaging apparatus 100 includes a pinion gear 82, a rack 84, and the like configured to vertically displace the elongated cylindrical portion 30b relative to the support leg portion 40. In other words, the breast imaging apparatus 100 includes the vertical-driving unit 116 for vertically displacing the gantry 30. A height of the opening 20 can be adjusted according to a height of the breast of the subject by vertically displacing the gantry 30. The rack and pinion method has been described as the vertical-driving unit 116 by way of example as described above, but the vertical-driving unit 116 may be embodied in another manner, such as a combination of a cam follower and a guide rail.

<Radiation Generation Unit and Radiation Detection Unit>

The breast imaging apparatus 100 includes the radiation generation unit 10 for generating the radiation, and the radiation detection unit 12 for detecting the radiation, generated by the radiation generation unit 10, with which the breast is irradiated, and can rotate the radiation generation unit 10 and the radiation detection unit 12 facing each other.

The radiation generation unit 10 and the radiation detection unit 12 are mounted on the rotational frame 38 that can rotate relative to the fixed frame 30a of the gantry 30. In the present exemplary embodiment, as illustrated in FIG. 3, the breast imaging apparatus 100 includes both of a radiation generation unit 10a and a radiation detection unit 12a for the CT imaging, and a radiation generation unit 10b and the radiation detection unit 12b for the mammographic imaging. The gantry 30 includes both of the radiation generation unit 10a and the radiation detection unit 12a for the CT imaging, and the radiation generation unit 10b and the radiation detection unit 12b for the mammographic imaging. In other words, the breast imaging apparatus 100 includes two pairs of radiation generation units and radiation detection units for the CT imaging and the mammographic imaging.

The gantry 30 includes the ring-shaped rotational frame 38 for rotating the radiation generation unit 10a and the radiation detection unit 12a for the CT imaging facing each other, and rotating the radiation generation unit 10b and the radiation detection unit 12b for the mammographic imaging facing each other.

More specifically, the radiation generation unit 10a and the radiation detection unit 12a are mounted on the rotational frame 38 for the CT imaging. The radiation detection unit 12a is mounted on the rotational frame 38 via the support base 2 supporting the radiation detection unit 12a.

The radiation generation unit 10b and the radiation detection unit 12b are mounted on the rotational frame 38 for the mammographic imaging. The radiation detection unit 12b is mounted on the rotational frame 38 via the support base 2.

The rotational frame 38 is coupled to the fixed frame 30a of the gantry 30 via a bearing having a bearing structure. The fixed frame 30a is kept in an immovable state, and is a stationary frame. The rotational frame 38 can be rotated by the rotational-driving unit 112. The rotational-driving unit 112 is mounted inside the gantry 30 so that the rotational axis of the rotational frame 38 extends in the horizontal direction.

Further, the pressing plate 14 is mounted on the support base 2 to be movable vertically. Further, a rotational tab 54, which is used to raise and lower the pressing plate 14, is provided on the support base 2. The breast of the subject can be sandwiched between the pressing plate 14 and the radiation detection unit 12b by rotating the rotational tab 54 to lower the pressing plate 14.

The rotational frame 38 includes cameras 80 (80a and 80b) and 81 so as to be able to capture a visible image with the breast sandwiched between the radiation detection unit 12b and the pressing plate 14 at the time of the mammographic imaging or the breast fixed in the breast holding portion 34 at the time of the CT imaging. Cameras 80a and 80b can be mounted on the rotational frame 38, and the camera 81 can be mounted on the radiation generation unit 10. Alternatively, the cameras 80 and 81 may be mounted an the fixed frame 30a. The cameras 80a, 80b, and 81 each acquire a confirmation image for confirming a position of the imaging target in an imaging area.

In this manner, the support base 2 is provided on the rotational frame 38, and supports the radiation detection unit 12a, the radiation detection unit 12b, and the pressing plate 14. The breast imaging apparatus 100 can rotate the radiation detection unit 12a and the radiation detection unit 12b by rotating the rotational frame 38 together with the support base 2 by the rotational-driving unit 112. Further, the breast imaging apparatus 100 can rotate the radiation generation unit 10a and the radiation generation unit 10b by rotating the rotational frame 38 by the rotational-driving unit 112.

The breast imaging apparatus 100 according to the present exemplary embodiment has been described as including the two pairs of radiation generation units and radiation detection units for the CT imaging and the mammographic imaging by way of example, but the breast imaging apparatus 100 can also realize the CT imaging and the mammographic imaging with use of one pair of radiation generation unit and radiation detection unit. More specifically, the breast imaging apparatus 100 is equipped with a displacement mechanism (not illustrated) for displacing the radiation generation unit and the radiation detection unit depending an the CT imaging or the mammographic imaging.

For example, in the CT imaging, the radiation generation unit 10a is displaced to a position illustrated in FIG. 3 and the radiation detection unit 12a is displaced to a position illustrated in FIG. 3. In the mammographic imaging, the radiation generation unit 10b is displaced to a position illustrated in FIG. 3 and the radiation detection unit 12b is displaced to a position illustrated in FIG. 3.

<Rotational Frame>

The breast imaging apparatus 100 includes the rotational-driving unit 112 for rotating the radiation generation unit 10 and toe radiation detection unit 12 via the rotational frame 38. The radiation generation unit 10 includes the radiation generation unit 10b for the mammographic imaging and the radiation generation unit 10a for the CT imaging inside the radiation generation unit 10.

FIG. 4 illustrates an arrangement in which the breast imaging apparatus 100 carries out the mammographic imaging in a craniocaudal (CC) manner (a craniocaudal direction: a craniocaudal view). A position of the rotational frame 38 is set so that the radiation generation unit 10b, the pressing plate 14, and the radiation detection unit 12b are aligned in the vertical direction.

Rotating the rotational tab 54 causes the pressing plate 14 to be displaced, and thereby can adjust a distance between the pressing plate 14 and the radiation detection unit 12b. The displacement of the pressing plate 14 allows the breast of the subject to be compressed. In the CC mammographic imaging illustrated in FIG. 4, the breast positioned between the pressing plate 14 and the radiation detection unit 12b is subjected to the radiographic imaging while being compressed between the pressing plate 14 and the radiation detection unit 12b.

The rotational-driving unit 112 is mounted inside the fixed frame 30a. The rotational frame 38 is rotatably connected to the rotational-driving unit 112 via a coupling member (e.g., a belt). Further, the bearing is set in a space between the fixed frame 30a and the rotational frame 38. The rotational frame 38 rotates relative to the fixed frame 30a by being driven by the rotational-driving unit 112.

Figure 7:
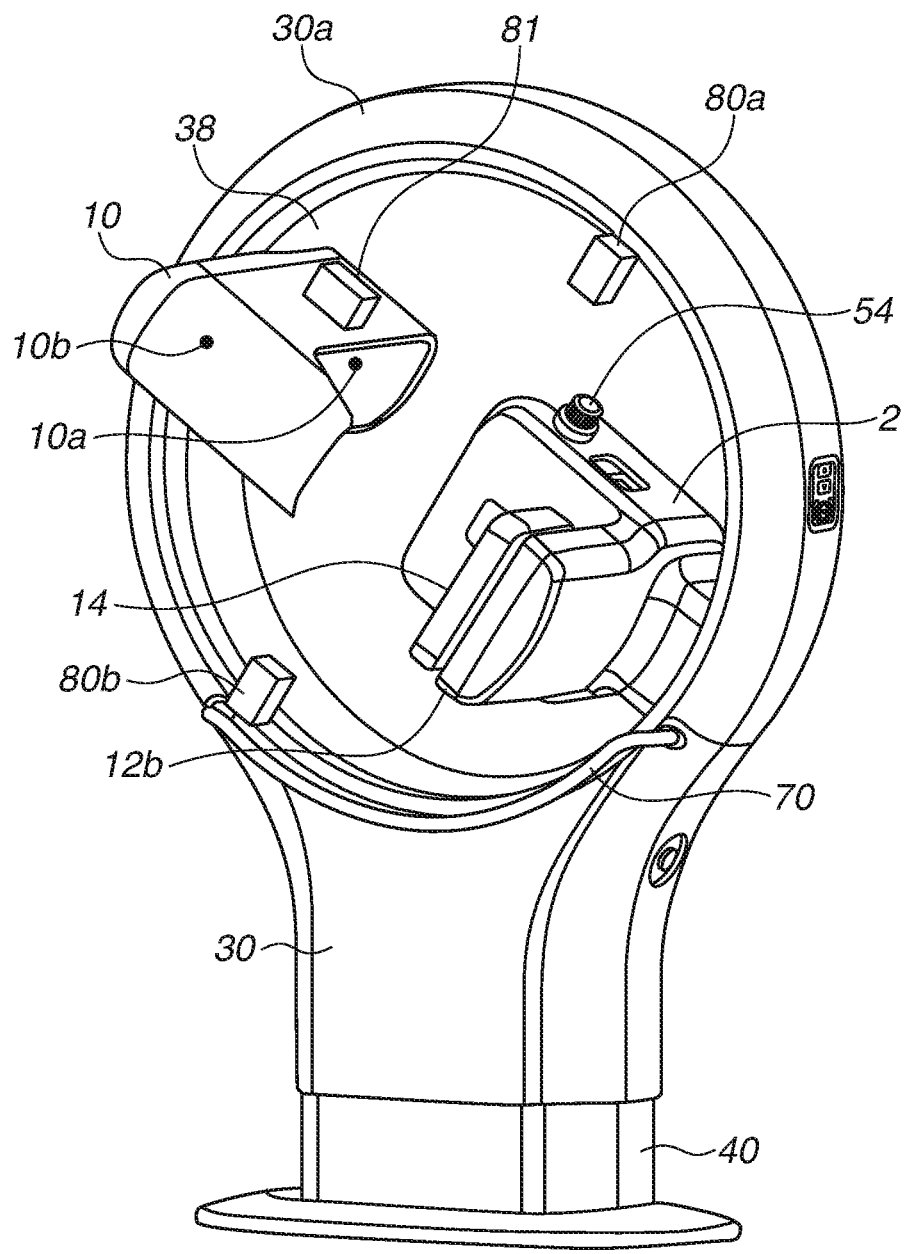
FIG. 7 illustrates a rotated state by a rotational-driving unit of the radiographic imaging apparatus according to the exemplary embodiment of the present invention.

FIG. 7 illustrates a rotated state in which the radiation generation unit 10b and the radiation detection unit 12b are rotated by the rotational-driving unit 112 of the breast imaging apparatus 100. When the breast imaging apparatus 100 carries out the mammographic imaging in a mediolateral oblique (MLO) manner (mediolateral oblique direction: a mediolateral oblique view), the rotational frame 38 is rotated by a predetermined angle (e.g., approximately 65 degrees) from the state illustrated in FIG. 4 and is then halted into a stopped state, as illustrated in FIG. 7.

The stopped state of the rotational frame 38 may be maintained with use of any a servo or a brake. In the MLO mammographic imaging illustrated in FIG. 7, the breast positioned between the pressing plate 14 and the radiation detection unit 12b is subjected to the radiographic imaging while being compressed between the pressing plate 14 and the radiation detection unit 12b.

Further, when the CT imaging is carried out, the rotational frame 38 is rotated relative to the fixed frame 30a by being driven by the rotational-driving unit 112. More specifically, the rotational frame 38 is rotated by at least 180 degrees. When the rotational frame 38 is being rotated, the radiation generation unit 10a generates the radiation, and the radiation detection unit 12a detects the radiation. The radiation detection unit 12 can carry out the CT imaging with respect to the breast of the subject by detecting the radiation transmitted through the breast of the subject. The breast imaging apparatus 100 can generate the CT image by reconstructing the captured radiation data.

<Gripping Portion>

As illustrated in FIG. 2, the plurality of gripping portions 22a, 22b, 22c, and 22d, which is used for the subject subjected to the CT imaging to hold them, is formed on the gantry 30 on the CT imaging side. More specifically, the plurality of gripping portions 22a, 22b, and 22d is each formed along a circumferential direction of an outer edge of the ring-shaped fixed frame 30a rotatably supporting the rotational frame 38 of the gantry 30. Further, the plurality of gripping portions 22a, 22b, 22c, and 22d is formed in proximity to a portion where the fixed frame 30a and the front cover 26 aced on the fixed frame 30a are joined to each other.

The gripping portion 22a, the gripping portion 22b, the gripping portion 22c, and the gripping portion 22d are provided on the fixed frame 30a at an upper right position, a lower right position, a lower left position, and an upper left position, respectively. The gripping portion may be provided on the fixed fame 30a at a top thereof, although this is not illustrated.

The plurality of ripping portions 22a, 22b, 22c, and 22d each is a recessed gripping portion, and is formed on the ring-shaped fixed frame 30a. The gripping portions are recessed enough to allow the subject to place subject's finger therein.

As illustrated in FIG. 4, the gripping portion 70, which is used for the subject subjected to the mammographic imaging to hold it, is provided on the gantry 30 on the mammographic imaging side. The gripping portion 70 is provided along the circumferential direction of the outer edge of the ring-shaped fixed frame 30a. More specifically, the gripping portion 70 is formed so as to protrude from two support points at the fixed frame 30a. The support points are located on a lower side of the fixed frame 30a. A distance between the two support points at the gripping portion 70 is longer than a width of the radiation generation unit 10b or the radiation detection unit 12b. Further, the distance between the two support points at the gripping portion 70 is Longer than a width of the support base 2.

The gripping portion 70 is a rod-like member, and is provided so as to have an arched shape connecting the two support points of the fixed frame 30a. The gripping portion is a member like a so-called handrail. The gripping portion 70 is curved. More specifically, the gripping portion 70 is curved downward. The gripping portion 70 is shaped in this manner to prevent the radiation generation unit 10 and the radiation detection unit 12 from interfering with (hitting) the gripping portion 70 even when the radiation generation unit 10 and the radiation detection unit 12 are rotated.

Further, there is a space between the fixed frame 30a and the gripping portion 70 at the arched portion. This space is approximately a few centimeters. Due to the existence of the space between the fixed frame 30a and the gripping portion 70 at the arched portion, the subject can grip the gripping portion 70 with both hands.

The CT imaging side should allow an upper body of the subject to be brought into close contact with the front cover 26, and allow the breast of the subject (imaging target) to be inserted from the opening 20 and fixed in the breast holding portion 34. Therefore, the gripping portions 22a, 22b, 22c, and 22d on the CT imaging side are each formed into the recessed shape so as not to protrude from the gantry 30 so that they do not interfere with the subject in close contact with the front cover 26.

<Operation Unit>

As illustrated in FIGS. 2 and 4, the operation unit 50, which is used to operate the breast imaging apparatus 100, is disposed on the gantry 30. The operation unit 50 is disposed on a non-rotational component of the breast imaging apparatus 100. The operation unit 50 is disposed on each of left and right side surfaces of the fixed frame 30a of the gantry 30.

More specifically, the operation unit 50 includes an operation unit 50a and an operation unit 50b. The operation unit 50a and the operation unit 50b are disposed at a right end and a left end of the fixed frame 30a, respectively. As illustrated in FIG. 5, the operation unit (operation unit 50a and operation unit 50b) is connected to the control unit 110.

As illustrated in FIG. 4, the operation unit 52, which is used to operate the breast imaging apparatus 100, is disposed on the support base 2 provided at the rotational frame 38. In other words, the operation unit 52 is disposed on a rotational component of the breast imaging apparatus 100. In the present exemplary embodiment, the operation unit 52 is disposed on left and right side surfaces of the support base 2. As illustrated in FIG. 5, the operation unit 52 is connected to the control unit 110.

The operation unit 50 disposed on the gantry 30 and the operation unit 52 disposed on the support base 2 have similar button configurations. The operation unit 50 and the operation unit 52 have similar functions. The operation unit 50 and the operation unit 52 each include a button for raising and lowering the pressing plate 14 and a button for rotating the radiation generation unit 10 and the radiation detection unit 12. These buttons can be pressed by an operator with the operator's finger.

Figure 8:
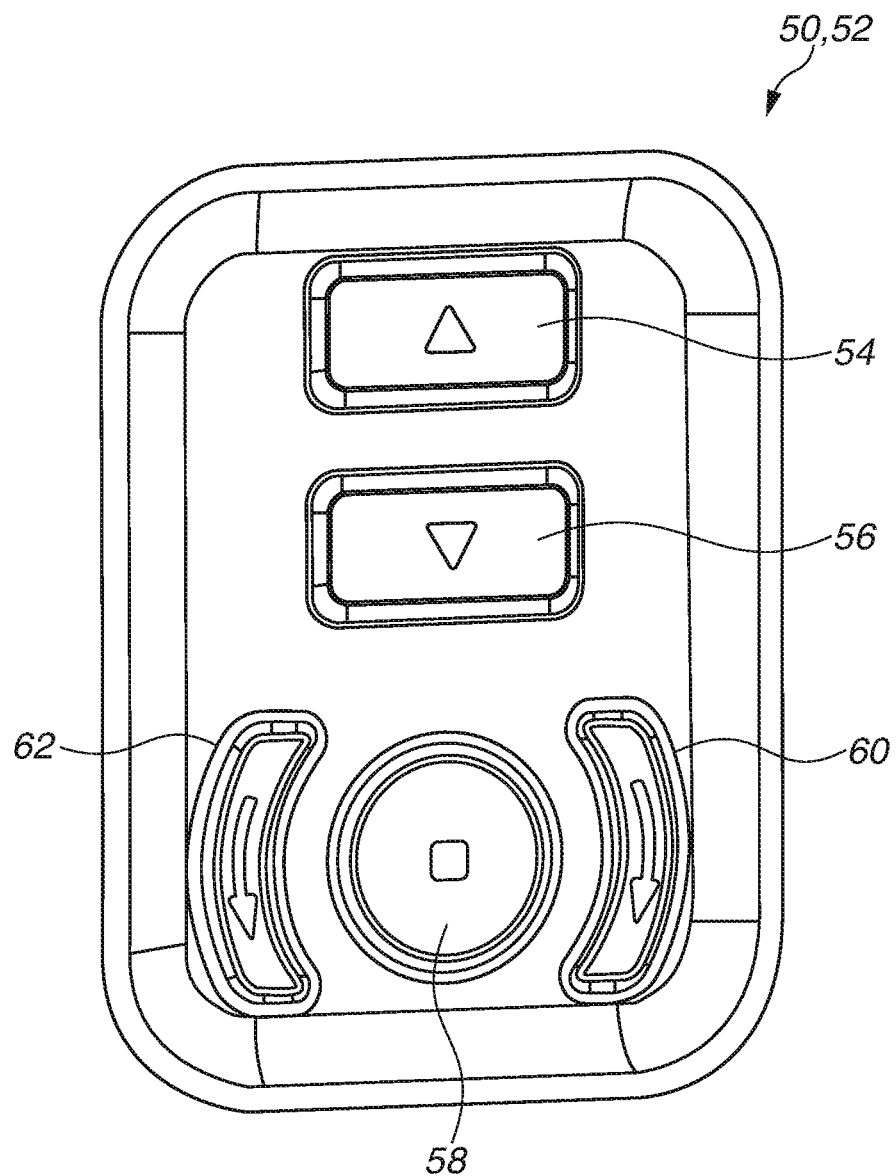
FIG. 8 illustrates a button configuration of an operation unit of the radiographic imaging apparatus according to the exemplary embodiment of the present invention.

FIG. 8 illustrates the button configuration each of the operation unit 50 and the operation unit 52. More specifically, the operation unit 50 and the operation unit 52 each include an up button 54, a down button 56, a home position button 58, a rightward rotation button 60, and a leftward rotation button 62. Each of the buttons is connected to the control unit 110, and can perform various kinds of control. The operation unit 50 and the operation unit 52 are used mainly at the time of the mammographic imaging.

The up button 54 is a button for displacing the pressing plate 14 upward (toward the radiation generation unit 10 side). The down button 56 is a button for displacing the pressing plate 14 downward (toward the radiation detection unit 12 side).

The rightward rotation button 60 is a button for rotating the rotational frame 38 to the right, thereby rotating the radiation generation unit 10 and the radiation detection unit 12 to the right. The leftward rotation button 62 is a button for rotating the rotational frame 38 to the left, thereby rotating the radiation generation unit 10 and the radiation detection unit 12 to the left.

When the operator presses the rightward rotation button 60, the control unit 110 rotates the radiation generation unit 10 and the radiation detection unit 12 to the right with use of the rotational-driving unit 112. More specifically, when the operator presses the rightward rotation button 60 once, the control unit 110 rotates the radiation generation unit 10 and the radiation detection unit 12 to the right by 360 degrees. Positions of the radiation generation unit 10 and the radiation detection unit 12 before the rotation, and positions of the radiation generation unit 10 and the radiation detection unit 12 after the rotation match each other, respectively.

Further, when the operator presses down the rightward rotation button 60 for a long time, the control unit 110 rotates the radiation generation unit 10 and the radiation detection unit 12 to the right at a low speed with use of the rotational-driving unit 112. The rotational speed at which the radiation generation unit 10 and the radiation detection unit 12 are rotated when the rightward rotation button 60 is pressed down for a long time is lower than a rotational speed at which they are rotated by 360 degrees as described above, and a rotational speed at which they are rotated at the time of the CT imaging. When the operator releases the operator's finger from the rightward rotation button 60, the control unit 110 halts the radiation generation unit 10 and the radiation detection unit 12 at this position, and the radiation generation unit 10 and the radiation detection unit 12 stop their rotations.

Similarly, when the operator presses the leftward rotation button 62, the control unit 110 rotates the radiation generation unit 10 and the radiation detection unit 12 to the left with use of the rotational-driving unit 112. More specifically, when the operator presses the leftward rotation button 62 once, the control unit 110 rotates the radiation generation unit 10 and the radiation detection unit 12 to the left by 360 degrees. Positions of the radiation generation unit 10 and the radiation detection unit 12 before the rotation, and positions of the radiation generation unit 10 and the radiation detection unit 12 after the rotation match each other, respectively.

Further, when the operator presses down the leftward rotation button 62 for a long time, the control unit 110 rotates the radiation generation unit 10 and the radiation detection unit 12 to the left at a low speed with use of the rotational-driving unit 112. When the operator releases the operator's finger from the leftward rotation button 62, the control unit 110 halts the radiation generation unit 10 and the radiation detection unit 12 at this position, and the radiation generation unit 10 and the radiation detection unit 12 stop their rotations.

Pressing down the rightward rotation button 60 or the leftward rotation button 62 for a long time is the most appropriate way to set angles of the radiation generation unit 10 and the radiation detection unit 12 in the mammographic imaging (MLO).

The home position button 58 is a button for rotating the radiation generation unit 10 and the radiation detection unit 12 to the right or the left, and displacing the radiation generation unit 10 to an upper position and the radiation detection unit 12 to a lower position as illustrated in FIG. 4. The home position is such a state that the radiation generation unit 10 and the radiation detection unit 12 are displaced to the upper position and the lower position, respectively, and is such a state that the radiation generation unit 10 and the radiation detection unit 12 are arranged in the perpendicular direction. The home position corresponds to a state of the CC imaging of the mammographic imaging.

Upon the pressing of the home position button 58, even when the radiation generation unit 10 and the radiation detection unit 12 are tilted, the control unit 110 rotates the radiation generation unit 10 and the radiation detection unit 12 so as to position at the home position with use of the rotational-driving unit 112. The control unit 110 rotates the radiation generation unit 10 and the radiation detection unit 12 to the right or the left at a low speed. The rotation leading to the home position is carried out at a lower speed than the rotational speed at which the radiation generation unit 10 and the radiation detection unit 12 are rotated by 360 degrees as described above, and the rotational speed at which the radiation generation unit 10 and the radiation detection unit 12 are rotated in the CT imaging.

The operation unit 50 may include a gantry up/down button for raising and lowering the gantry 30. When the gantry up/down button is pressed, the control unit 110 can vertically displace the gantry 30 with use of the above-described vertical-driving unit 116. A height of the gantry 30 can be adjusted in conformity with a height of the subject.

In this manner, the first operation unit 50, which is used to operate the breast imaging apparatus 100, is disposed on the gantry 30 of the breast imaging apparatus 100 according to the present exemplary embodiment, and the second operation unit 52, which has the similar function to the first operation unit 50, is disposed on the support base 2 supporting the radiation detection unit 12.

Therefore, the operator can operate the breast imaging apparatus 100 with use of the operation unit of the breast imaging apparatus 100 according to the image capturing mode of the subject.

<Console>

Figure 9:
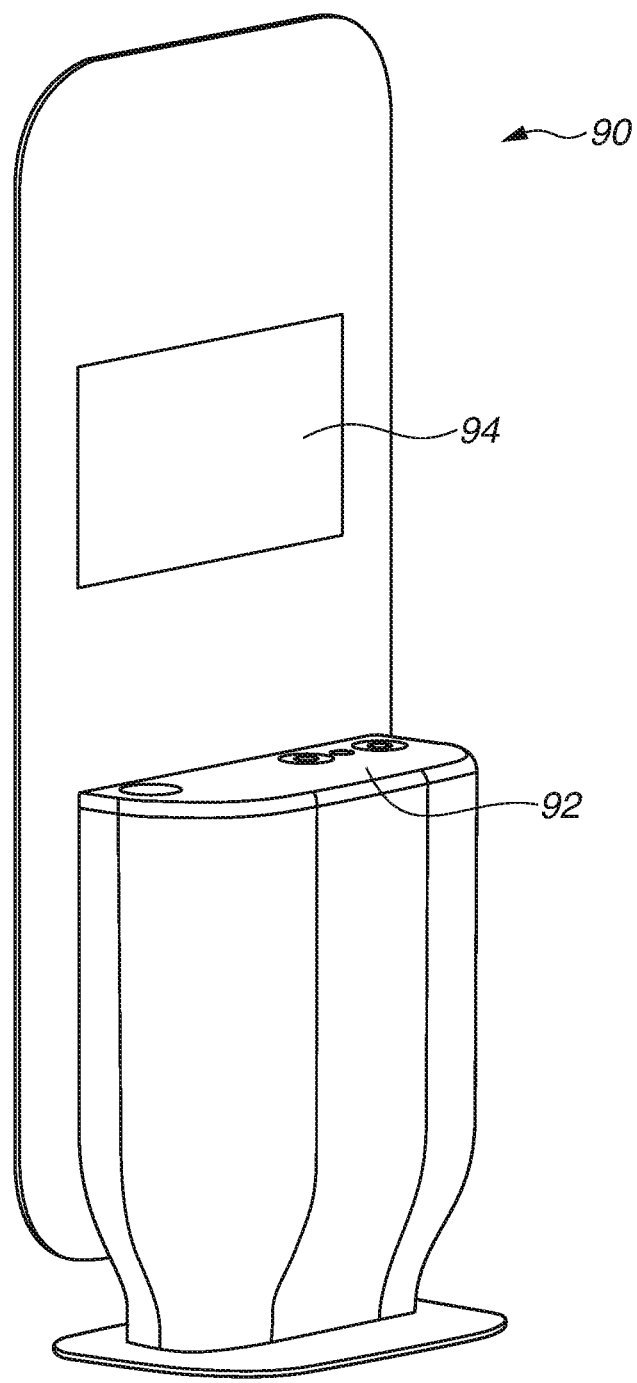
FIG. 9 illustrates a console of the radiographic imaging apparatus according to the exemplary embodiment of the present invention.

FIG. 9 illustrates the console 90 operated by the operator. The console 90 is set up outside the imaging room. The console 90 includes a button unit 92 and a display unit 94. The button unit 92 includes a button for raising and lowering the pressing plate 14, and a button for rotating the radiation generation unit 10 and the radiation detection unit 12, similarly to the operation unit 50 and the operation unit 52. As illustrated in FIG. 5, the console 90 is connected to the control unit 110.

The control unit (image control unit) 110 causes the display unit 94 configured to display a plurality of divided screens thereon to display a first radiographic image of a first imaging target (or portion) (e.g., left breast) on a first divided screen. Further, the control unit 110 causes a radiographic image of the first imaging target (portion) that is captured at a different time from the first radiographic image or a radiographic image of a second imaging target (or portion) (e.g., right breast) that is a symmetric imaging target of the first imaging target to be displayed on a second divided screen as a second radiographic image.

Differences of the console 90 from the operation unit 50 and the operation unit 52 are the provisions of a button regarding the CT imaging and the display unit 94. While a button regarding the mammographic imaging is prepared on the operation unit 50 and the operation unit 52, a button regarding the mammographic imaging and the button regarding the CT imaging are prepared on the console 90.

When the button regarding the CT imaging prepared on the console 90 is pressed, the control unit 110 can carry out the CT imaging while rotating the radiation generation unit 10 and the radiation detection unit 12.

Further, as described above, the breast imaging apparatus 100 can carry out the mammographic imaging with the breast of the subject sandwiched between the pressing plate 14 and the radiation detection unit 12. The control unit 110 of the breast imaging apparatus 100 generates the mammographic image based on the captured radiation data. The display unit 94 of the console 90 displays the generated mammographic image thereon.

Further, the breast imaging apparatus 100 can carry out the CT imaging by rotating the radiation generation unit 10 and the radiation detection unit 12. The control unit 110 of the breast imaging apparatus 100 can generate the CT image by reconstructing the captured radiation data. The display unit 94 of the console 90 displays the generated CT image thereon. In this manner, the display unit 94 displays thereon the radiographic image (mammographic image and CT image) generated based on the radiation data (detection data) of the radiation detection unit 12.

<Operation Screen>

Figure 10:
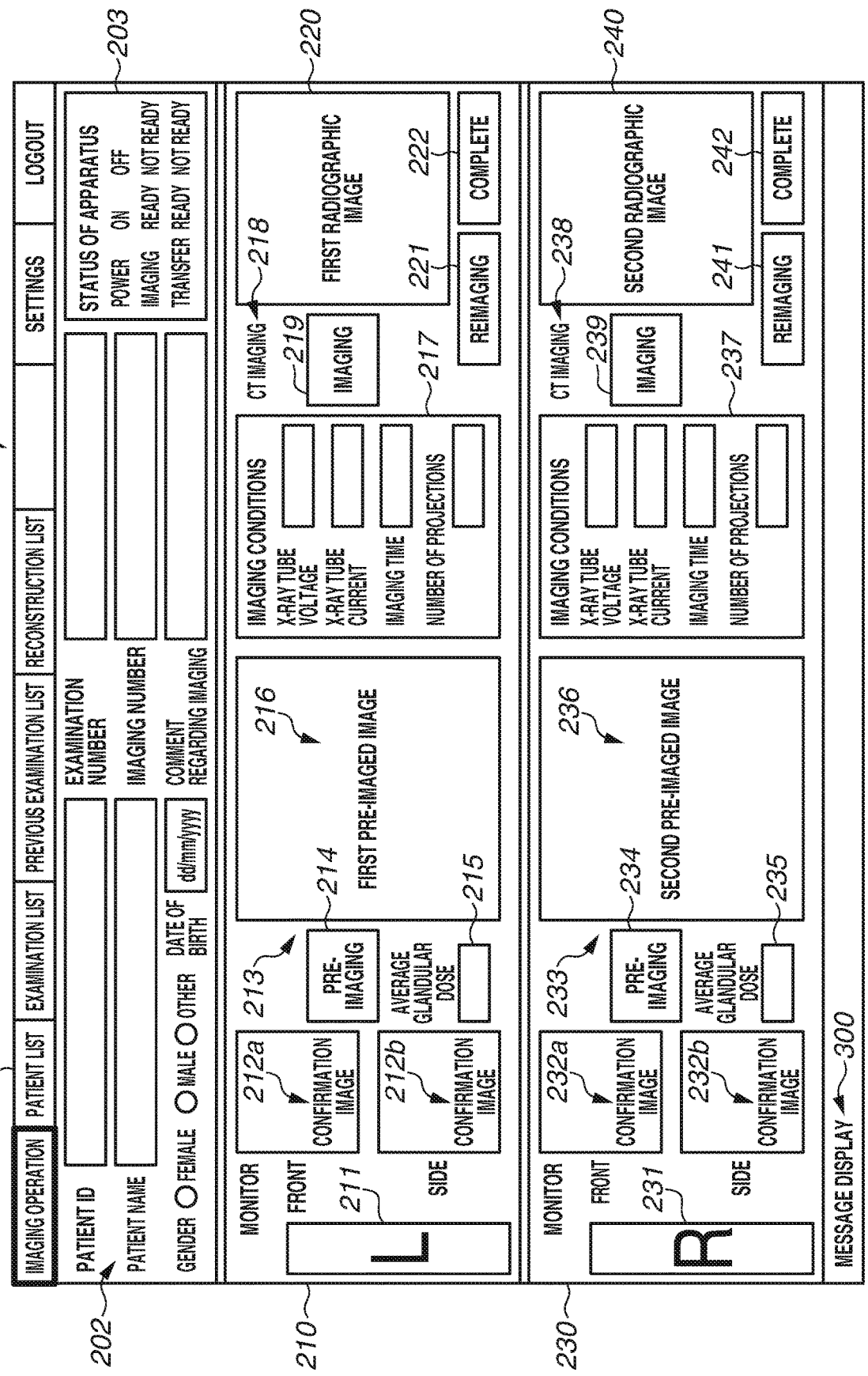
FIG. 10 illustrates an operation screen in a case where a comparative radiological interpretation of symmetric imaging targets is performed.

FIG. 10 illustrates an example of an imaging operation screen 200 when the CT imaging is carried out. As illustrated in FIG. 10, when the radiographic image is displayed on the display unit 94, the image division unit 500 causes the display unit 94 that displays the radiographic image thereon to display a plurality of divided screens (operation screen 210 and operation screen 230) thereon. The first image control unit 501 causes a radiographic image 220 (first radiographic image) of the left breast (first imaging target) to be displayed on the operation screen 210 (first divided screen). The second image control unit 502 causes a radiographic image 240 of the right breast (second imaging target) that is the symmetric imaging target of the left breast (first imaging target) to be displayed on the operation screen 230 (second divided screen) as the second radiographic image.

In the present exemplary embodiment, the first image control unit 501 causes the radiographic image 220 (first radiographic image) of the left breast (first imaging target) to be displayed on the operation screen 210 (first divided screen). The second image control unit 502 causes the radiographic image 240 of the right breast (opposite breast, i.e., second imaging target) to be displayed on the operation screen 230 (second divided screen) as the second radiographic image.

In the present exemplary embodiment, the left breast and the right breast, which are the symmetric imaging targets, are handled as the first imaging target and the second imaging target, respectively, but the symmetric imaging targets may be four limbs, fingers, lungs, or the like, other than the breasts. Further, radiographic images of the same portion or imaging target (e.g., left breast, chest, and abdomen) that are captured at different times may be displayed on the first divided screen and the second divided screen, respectively, as will be described below.

Operation tags 201 are displayed at a top of the screen 200, and a transition to a screen associated with each of the tags 201 is managed based thereon. An input screen 202 for inputting subject information is prepared under each of the tags 201 an the imaging operation screen 200, and this input screen 202 includes sections for inputting a patient identification (ID), a patient name, a gender, a date of birth, an examination number (No.), an imaging No., a comment regarding, the imaging. Upon an input of the patient ID, if there is information associated with the patient ID in advance, the information such as the patient name, the gender, and the date of birth associated therewith may be automatically input. For the examination No. and the imaging No., a unique number may be automatically input every time the examination is conducted.

Further, an apparatus status 203 is displayed to the right of the screen 202 for inputting the subject information. The operation screen 210 and the operation screen 230 for the CT examination are displayed arranged one above the other with similar configurations. In FIG. 10, an L display 211 indicating the left breast (first imaging target) is displayed in the operation screen 210, and an R display 231 indicating the right breast (second imaging target) is displayed in the operation screen 230. However, which imaging target is displayed on the left and the right is arbitrarily set according to an imaging order or the like.

Confirmation images (first confirmation images) of the left breast (first imaging target) that are captured by a camera 80 and a camera 81 in the imaging area are displayed on a monitor display 212*a* and a monitor display 212*b* in real time. Confirmation images (second confirmation images) of the right breast (the second imaging target) that are captured by the camera 80 and the camera 81 in the imaging area are displayed on a monitor display 232*a* and a monitor display 232*b* in real time. In other words, the first confirmation images are real-time optical images of the first imaging target, and the second confirmation images are real-time optical images of the second imaging target.

In this manner, the first image control unit 501 causes the first confirmation images for confirming the position of the left breast (first imaging target) to be displayed on the first divided screen, and the second image control unit 502 causes the second confirmation images for confirming the position of the right breast (second imaging target) to be displayed on the second divided screen.

The camera 80 and the camera 81 may be fixed to any of the radiation generation unit 10, the rotational frame 38, and the fixed frame 30*a*. Further, a camera for capturing the image from the front side of the breast may be mounted on the fixed frame 30*a* or the support base 2. Further, the camera 80 and the camera 81 may be attached on different structures, such as attaching the camera 81 for capturing the image from the side surface at the rotational frame 38.

A pre-imaging operation screen 213 and a pre-imaging operation screen 233 are operation units for preliminary imaging called pre-imaging for determining the imaging conditions of the CT imaging. The pre-imaging operation screens 213 and the Pre-imaging operation screen 233 include a pre-imaging button 214 and a pre-imaging button 234, an average glandular dose display 215 and an average glandular dose display 235, and a pre-imaged image 216 and a pre-imaged image 236, respectively. The breast is imaged for one screen (pre-imaged image) after being fixed, and the irradiation conditions of the CT imaging to be carried out next are determined based on the imaged signal. Further, at this time, a prediction value of an average glandular dose to be supplied to a mammary grand of the subject is calculated based on information of the pre-imaging, and the predicted average glandular dose is displayed on the average glandular dose display 215 or the average glandular dose display 235.

In this manner, the first image control unit 501 causes the pre-imaged image (first pre-imaged image) for setting the imaging conditions (first imaging conditions) of the radiographic image 220 (first radiographic image) of the left imaging target to be displayed on the operation screen 210 (first divided screen). The second image control unit 502 causes the pre-imaged image (second pre-imaged image) for setting the imaging conditions (second imaging conditions) of the radiographic image 240 (second radiographic image) of the right imaging target to be displayed on the operation screen 230 (second divided screen).

Further, the first image control unit 501 causes a first average dose of the pre-imaged image 216 (first pre-imaged image) of the left breast to be displayed on the operation screen 210 (first divided screen). The second image control unit 502 causes a second average dose of the pre-imaged image 236 (second pre-imaged image) of the right breast to be displayed on the operation screen 230 (second divided screen).

An imaging condition setting screen 217 and an imaging condition setting screen 237 display thereon values acquired by calculating optimum conditions based on the information of the pre-imaging. Further, the imaging conditions can also be changed on these screens.

In this manner, the first image control unit 501 causes the imaging conditions (first imaging conditions) of the radiographic image 220 (first radiographic image) of the left imaging target to be displayed on the operation screen 210 (first divided screen). The second image control unit 502 causes the imaging conditions (second imaging conditions) of the radiographic image 240 (second radiographic image) of the right imaging target to be displayed on the operation screen 230 (second divided screen).

Further, the display 211 and the display 231 respectively indicating the first and second imaging targets, the first pre-imaged image 216 and the second pre-imaged image 236, the first imaging condition 217 and second imaging condition 237, and the first radiographic image 220 and the second radiographic image 240 are displayed at substantially the same positions on the first and second divided screens, respectively.

Further, the first confirmation image and second confirmation image (monitor display 212 and monitor display 232) and the first average dose and second average dose (average glandular dose display 215 and average glandular dose display 235) are displayed at substantially the same positions on the first divided screen and second divided screen (operation screen 210 and operation screen 230), respectively.

Further, the display 211 and the display 231 respectively indicating the first and second imaging target, the first confirmation image 212 and second confirmation image 232, the first average dose 215 and second average dose 235, the first pre-imaged image 216 and second pre-imaged image 236, the first imaging condition 217 and second imaging condition 237, and the first radiographic image 220 and second radiographic image 240 are displayed on the first divided screen and second divided screen, respectively, in this order.

The CT imaging is operated and is monitored during the imaging on CT imaging operation screen 218 and CT imaging operation screen 238. The CT imaging operation screen 218 and the CT imaging operation screen 238 include an imaging button 219 and an imaging button 239, the radiographic image 220 and the radiographic image 240, a reimaging button 221 and a reimaging button 241, and a completion button 222 and a completion button 242, respectively.

After making a correction to the irradiation condition values calculated based on the pre-imaging information if necessary, the operator can confirm that the imaging can be carried out in a stable state by confirming the monitor display 212*a* and the monitor display 212*b* and/or directly observing the subject. After the confirmation, the CT imaging is carried out by operating the imaging button 219. Each of the images during the imaging is displayed on the radiographic image 220 or the radiographic image 240 in real time. During the imaging, the imaging button 219 or the imaging button 239 is turned into an interrupt button, and the imaging can be canceled by operating the interrupt button if necessary.

After completion of the imaging, the operator confirms one or both of the captured image displayed in real time and the reconstructed CT image, and operates the reimaging button 221 or the reimaging button 242 if necessary, by which reimaging is carried out. If the imaging is ended without a problem, the imaging is completed by operating the completion button 222 or the completion button 242.

After the end of the operation on the operation screen 210 or the operation screen 230, the information of the already carried out imaging is continuously displayed on the monitor displays 212*a*, 212 *b*, 232*a*, and 232*b*, the pre-imaging screen 216 and the pre-imaging screen 236, the imaging condition setting screens 217 and 237, and the radiographic image 220 and the radiographic image 240. A representative image may be displayed or a moving image may be displayed on the monitor displays 212*a*, 212 *b*, 232*a*, and 232*b*, and the radiographic image 220 and the radiographic image 240. The display of the radiographic image 220 (first radiographic image) of the left breast (first imaging target) may be changed in synchronization with the radiographic image 240 (second radiographic image) of the right breast (second imaging target).

Further, the displays may be arranged in a reverse order according to the rotation method in the CT, and the display order may be changed according to a position where the CT imaging is started, as necessary. When the monitor displays 212*a*, 212*b*, 232*a*, and 232*b*, and the radiographic image 220 and the radiographic image 240 are displayed, the left side and the right side or the upper side and the lower side of the display may be inverted so as to facilitate the imaging and adjustment of the positions of the symmetric imaging targets.

In the above-described manner, according to the present exemplary embodiment, the breast imaging apparatus 100 can facilitate a comparative radiological interpretation of the symmetric imaging targets by dividing the operation screen of the breast imaging apparatus 100 into the plurality of divided screens and causing the displays indicating the imaging targets, the pre-imaged images, the imaging conditions, the radiographic images, and the like to be displayed on the divided screens, respectively. Further, the present exemplary embodiment allows the breast imaging apparatus 100 to aid the imaging by the operator by causing the displays indicating the imaging targets, the pre-imaged images, the imaging conditions, the radiographic images, and the like to be displayed on the divided screens, respectively, according to a processing procedure for imaging the radiographic images. Further, the present exemplary embodiment allows the breast imaging apparatus 100 to aid the imaging by the operator by displaying the imaging conditions of the opposite imaging target serving as a reference at the same time as the current imaging.

Although the exemplary embodiment of the present invention has been described above, the present invention is not limited thereto and can be changed or modified within a range defined in the claims.

Figure 11:
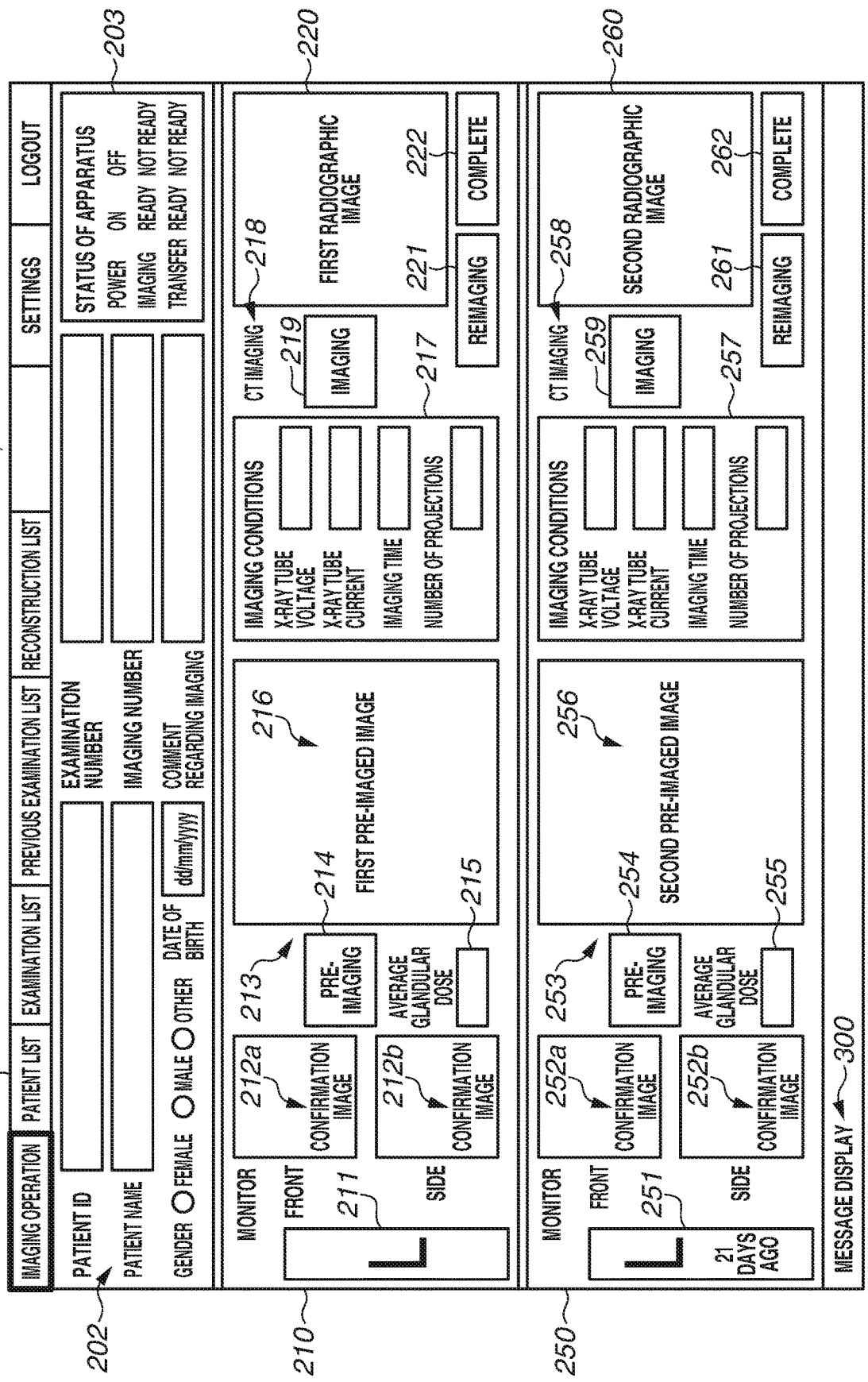
FIG. 11 illustrates an operation screen in a case where a temporal-change comparative radiological interpretation of a same imaging target is performed.

For example, the breast imaging apparatus may cause the radiographic images of the same imaging target (e.g., left breast, chest, and abdomen) that are captured at different times to be displayed on the first divided screen and the second divided screen, respectively. FIG. 11 illustrates an example in which the breast imaging apparatus causes the radiographic images of the left breast that are captured at different times to be displayed on the first divided screen and the second divided screen, respectively.

This breast imaging apparatus causes the current imaging information of the same imaging target (e.g., left breast) of the same subject to be displayed on an operation screen 250 (second divided screen), instead of the imaging information of the opposite right breast that is the symmetric imaging target. At this time, the operator may select an optimum previous examination from a previous examination list on the operation tag 201, and cause previous imaging information of the left breast of the same subject to be displayed on the operation screen 210. Alternatively, the breast imaging apparatus may automatically select the most recent examination, and automatically cause the most recent imaging information of the left breast of the same subject to be displayed on the operation screen 210 (first divided screen).

Further, an imaging date and time or an imaging time interval may be displayed in the L display 211 when the previous imaging information is referred to.

In this manner, the second image control unit 502 causes a radiographic image 260 of the left breast (first imaging target) that is captured at a different time from the radiographic image 220 (first radiographic image) of the left breast (first imaging target) to be displayed on the operation screen 250 (second divided screen) as the second radiographic image.

Further, the radiographic images captured at the different imaging times or the like may be displayed on the plurality of divided screens in combination with the imaging of the symmetric imaging targets (left and right breasts) described. In the above-described exemplary embodiment. In this case, the radiographic images of the different imaging targets and the different imaging times or the like may be displayed on three or more divided screens, respectively, or the radiographic images may be displayed while a radiographic image to be displayed or the like is switched when necessary.

The breast imaging apparatus can facilitate a temporal comparative radiological interpretation of the same imaging target by dividing the operation screen of the breast imaging apparatus into the plurality of divided screens and causing the displays indicating the same imaging target, the pre-imaged imaged images, the imaging conditions, the radiographic images, and the like to be displayed on the divided screens, respectively. Further, this configuration allows the breast imaging apparatus to aid the imaging by the operator by causing the displays indicating the same imaging target, the pre-imaged imaged images, the imaging conditions, the radiographic images, and the like to be displayed on the divided screens, respectively, according to the processing procedure for imaging the radiographic images. Further, this configuration allows the breast imaging apparatus to aid the imaging by the operator by displaying the previous imaging conditions serving as a reference at the same time as the current imaging.

Further, the number of screens into which the operation screen is divided may be four screens or more so as to allow the operator to compare, for example, the radiographic images of the symmetric imaging targets (left and right breasts) and the different imaging times.

Further, the first image control unit 501 may cause the radiographic image captured by the mammographic imaging of the breast to be displayed on the first divided screen as the first radiographic image, and the second image control unit 502 may cause the radiographic image captured by the CT imaging of the breast to be displayed on the second divided screen as the second radiographic image. This display allows the operator to refer to the radiographic image captured by the mammographic imaging, thereby taking a lesion position into consideration when the breast is imaged by the CT imaging.

Further, at least one of a hue, a brightness, a color saturation, and a color scheme may be different between the first and second divided screens. This difference allows the breast imaging apparatus to improve visibility of each of the divided screens.

The present invention may also be embodied by supplying software (program) capable of realizing the function of the above-described exemplary embodiment to a system or an apparatus via a network or various types of storage media, and causing a computer (central processing unit (CPU), micro processing unit (MPU), or the like) of the system or the apparatus to read out the program. Further, the present invention can also be realized by processing in which one or more processor(s) in the computer of the system or the apparatus read(s) out and execute(s) the program, and can also be realized by a circuit (e.g., an application specific integrated circuit (ASIC)) capable of realizing one or more function(s).

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-123372, filed Jun. 22, 2016, which is hereby incorporated by reference herein in its entirety.

What is claimed is:

1. A radiographic imaging apparatus comprising:
an image control unit configured to cause a display unit that displays a plurality of divided screens to display a first radiographic image of a first imaging target on a first divided screen of the plurality of divided screens,
wherein the image control unit:
causes a radiographic image of the first imaging target that is captured at a different time from the first radiographic image or a radiographic image of a second imaging target that is a symmetric portion of the first imaging target to be displayed on a second divided screen of the plurality of divided screens as a second radiographic image,
causes at least one of a first confirmation image for confirming a position of the first imaging target and a first average dose of a first pre-imaged image to be displayed on the first divided screen, and
causes at least one of a second confirmation image for confirming a position of the second imaging target and a second average dose of a second pre-imaged image to be displayed on the second divided screen.

2. The radiographic imaging apparatus according to claim 1,
wherein the first imaging target is a breast of a subject and the first radiographic image is a radiographic image of the breast, and
wherein the second radiographic image is a radiographic image of the breast that is captured at the different time from the first radiographic image, or a radiographic image of an opposite breast of the subject that is the second imaging target.

3. The radiographic imaging apparatus according to claim 1,
wherein the image control unit causes at least one of a first pre-imaged image for setting a first imaging condition of the first radiographic image and the first imaging condition to be displayed on the first divided screen, and
wherein the image control unit causes at least one of a second pre-imaged image for setting a second imaging condition of the second radiographic image and the second imaging condition to be displayed on the second divided screen.

4. The radiographic imaging apparatus according to claim 3, wherein displays respectively indicating the first imaging target and second imaging target, the first pre-imaged image and the second pre-imaged image, the first imaging condition and the second imaging condition, and the first radiographic image and the second radiographic image are displayed at substantially same positions on the first divided screen and the second divided screen, respectively.

5. The radiographic imaging apparatus according to claim 3, wherein displays respectively indicating the first imaging target and the second imaging target, the first pre-imaged image and the second pre-imaged image, the first imaging condition and the second imaging condition, and the first radiographic image and the second radiographic image are displayed on the first divided screen and the second divided screen, respectively, in an order of the displays respectively indicating the first imaging target and the second imaging target, the first pre-imaged image and the second pre-imaged image, the first imaging condition and the second imaging condition, and the first radiographic image and the second radiographic image.

6. The radiographic imaging apparatus according to claim 1, wherein displays respectively indicating the first imaging target and the second imaging target, the first confirmation image and the second confirmation image, the first average dose and the second average dose, the first pre-imaged image and the second pre-imaged image, a first imaging condition and a second imaging condition, and the first radiographic image and the second radiographic image are displayed at substantially same positions on the first divided screen and the second divided screen, respectively.

7. The radiographic imaging apparatus according to claim 1, wherein displays respectively indicating the first imaging target and the second imaging target, the first confirmation image and the second confirmation image, the first average dose and the second average dose, the first pre-imaged image and the second pre-imaged image, a first imaging condition and a second imaging condition, and the first radiographic image and the second radiographic image are displayed on the first divided screen and the second divided screen, respectively, in an order of the displays respectively indicating the first imaging target and the second imaging target, the first confirmation image and the second confirmation image, the first average dose and the second average dose, the first pre-imaged image and the second pre-imaged image, the first imaging condition and the second imaging condition, and the first radiographic image and the second radiographic image.

8. The radiographic imaging apparatus according to claim 1, wherein the first confirmation image is a real-time optical image of the first imaging target, and the second confirmation image is a real-time optical image of the second imaging target.

9. The radiographic imaging apparatus according to claim 1,
wherein the image control unit causes a radiographic image captured by mammographic imaging of a breast of a subject to be displayed on the first divided screen as the first radiographic image, and
wherein the image control unit causes a radiographic image captured by CT imaging of the breast to be displayed on the second divided screen as the second radiographic image.

10. The radiographic imaging apparatus according to claim 1, wherein at least one of a hue, a brightness, a color saturation, and a color scheme is different between the first divided screen and the second divided screen.

11. A radiographic imaging system comprising:
a radiation generation unit configured to generate radiation;
a radiation detection unit configured to detect the radiation;
a rotational unit configured to rotate the radiation generation unit and the radiation detection unit facing each other;
an image division unit configured to cause a display unit to display a plurality of divided screens, the display unit being configured to display thereon a radiographic image generated based on detection data of the radiation detection unit;
a first image control unit configured to cause a first radiographic image of a first imaging target to be displayed on a first divided screen of the plurality of divided screens, and to cause at least one of a first confirmation image for confirming a position of the first imaging target and a first average dose of a first pre-imaged image to be displayed on the first divided screen; and
a second image control unit configured to cause a radiographic image of the first imaging target that is captured at a different time from the first radiographic image or a radiographic image of a second imaging target that is a symmetric portion of the first imaging target to be displayed on a second divided screen of the plurality of divided screens as a second radiographic image, and to cause at least one of a second confirmation image for confirming a position of the second imaging target and a second average dose of a second pre-imaged image to be displayed on the second divided screen.

12. A radiographic imaging method comprising:
causing a display unit configured to display a radiographic image to display a plurality of divided screens;
causing a first radiographic image of a first imaging target to be displayed on a first divided screen of the plurality of divided screens;
causing a radiographic image of the first imaging target that is captured at a different time from the first radiographic image or a radiographic image of a second imaging target that is a symmetric imaging target of the first imaging target to be displayed on a second divided screen of the plurality of divided screens as a second radiographic image;
causing at least one of a first confirmation image for confirming a position of the first imaging target and a first average dose of a first pre-imaged image to be displayed on the first divided screen; and
causing at least one of a second confirmation image for confirming a position of the second imaging target and a second average dose of a second pre-imaged image to be displayed on the second divided screen.

13. A non-transitory computer-readable storage medium storing a program for causing a computer to perform a radiographic imaging method, the radiographic imaging method comprising:
causing a display unit configured to display a radiographic image to display a plurality of divided screens thereon;
causing a first radiographic image of a first imaging target to be displayed on a first divided screen of the plurality of divided screens;
causing a radiographic image of the first imaging target that is captured at a different time from the first radiographic image or a radiographic image of a second imaging target that is a symmetric portion of the first imaging target to be displayed on a second divided screen of the plurality of divided screens as a second radiographic image;
causing at least one of a first confirmation image for confirming a position of the first imaging target and a first average dose of a first pre-imaged image to be displayed on the first divided screen; and
causing at least one of a second confirmation image for confirming a position of the second imaging target and a second average dose of a second pre-imaged image to be displayed on the second divided screen.

* * * * *